United States Patent
Sherman

[11] Patent Number: 5,954,704
[45] Date of Patent: Sep. 21, 1999

[54] ASPIRATOR FIXTURE FOR AMBULANCES

[75] Inventor: Leslie H. Sherman, Denville, N.J.

[73] Assignee: Impact Instrumentation, Inc., West Caldwell, N.J.

[21] Appl. No.: 08/880,931

[22] Filed: Jun. 23, 1997

[51] Int. Cl.[6] ............................ A61M 1/00; A61M 15/00
[52] U.S. Cl. ...................... 604/319; 604/322; 128/200.24
[58] Field of Search ..................................... 604/118, 119, 604/319–323, 35, 131; 128/200.24, 205.12; 15/339, 344

[56] References Cited

U.S. PATENT DOCUMENTS

| | | | |
|---|---|---|---|
| Re. 33,250 | 7/1990 | Cook | 604/317 |
| 3,915,189 | 10/1975 | Holbrook et al. | 604/319 |
| 4,033,511 | 7/1977 | Chamberlin | 239/346 |
| 4,934,020 | 6/1990 | Jackson | 15/339 |
| 5,065,745 | 11/1991 | Meier | 128/205.12 |
| 5,134,994 | 8/1992 | Say | 128/200.24 |
| 5,449,347 | 9/1995 | Preen et al. | 604/118 |
| 5,466,229 | 11/1995 | Elson et al. | 604/317 |
| 5,662,627 | 9/1997 | Say | 604/319 |
| 5,683,371 | 11/1997 | Hand | 604/317 |
| 5,776,119 | 7/1998 | Bilbo et al. | 604/317 |

*Primary Examiner*—Ronald Stright
*Assistant Examiner*—David J. Cho
*Attorney, Agent, or Firm*—Arthur G. Yeager

[57] ABSTRACT

A fixture includes aspirator components that are compactly oriented and mounted in a housing that is attachable to the interior wall of ambulance. The housed components include a diaphragm pump, a DC motor, a valve for regulating the fluid intake to the pump, and a gauge displaying vacuum conditions. A multipanel housing structure defines a cavity in which the components are mounted and it has angularly arranged panels that facilitate a compact component arrangement in the cavity with the vacuum gauge display, and gas valve and electrical switch controls being conveniently located at the exterior of the housing. The electrical connection with the 12 V DC ambulance power source avoids the presence of electrical conductors in the patient transport area and a bracket for supporting canisters used in the aspirator systems at the exterior of the fixture is also such as to avoid the presence in the action area of unnecessary conduits and containers with electrically conductive fluids.

15 Claims, 6 Drawing Sheets

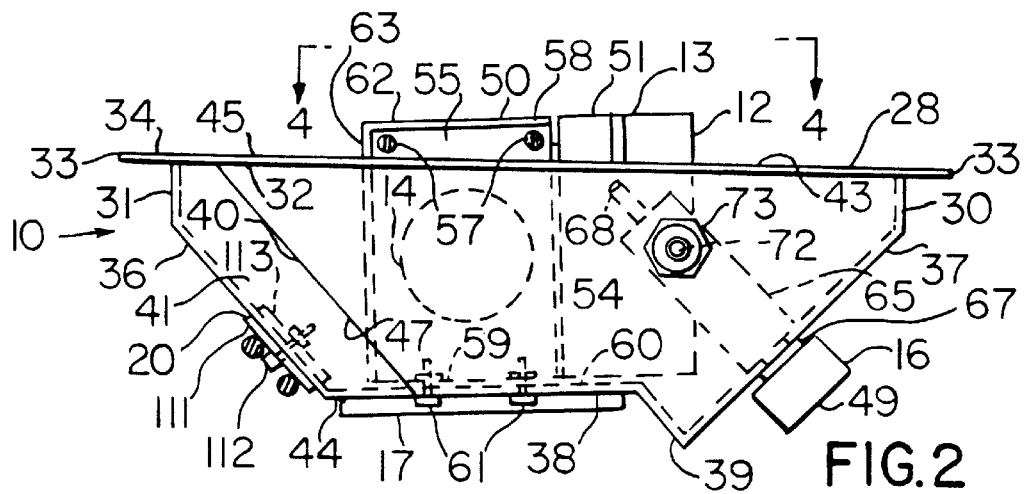
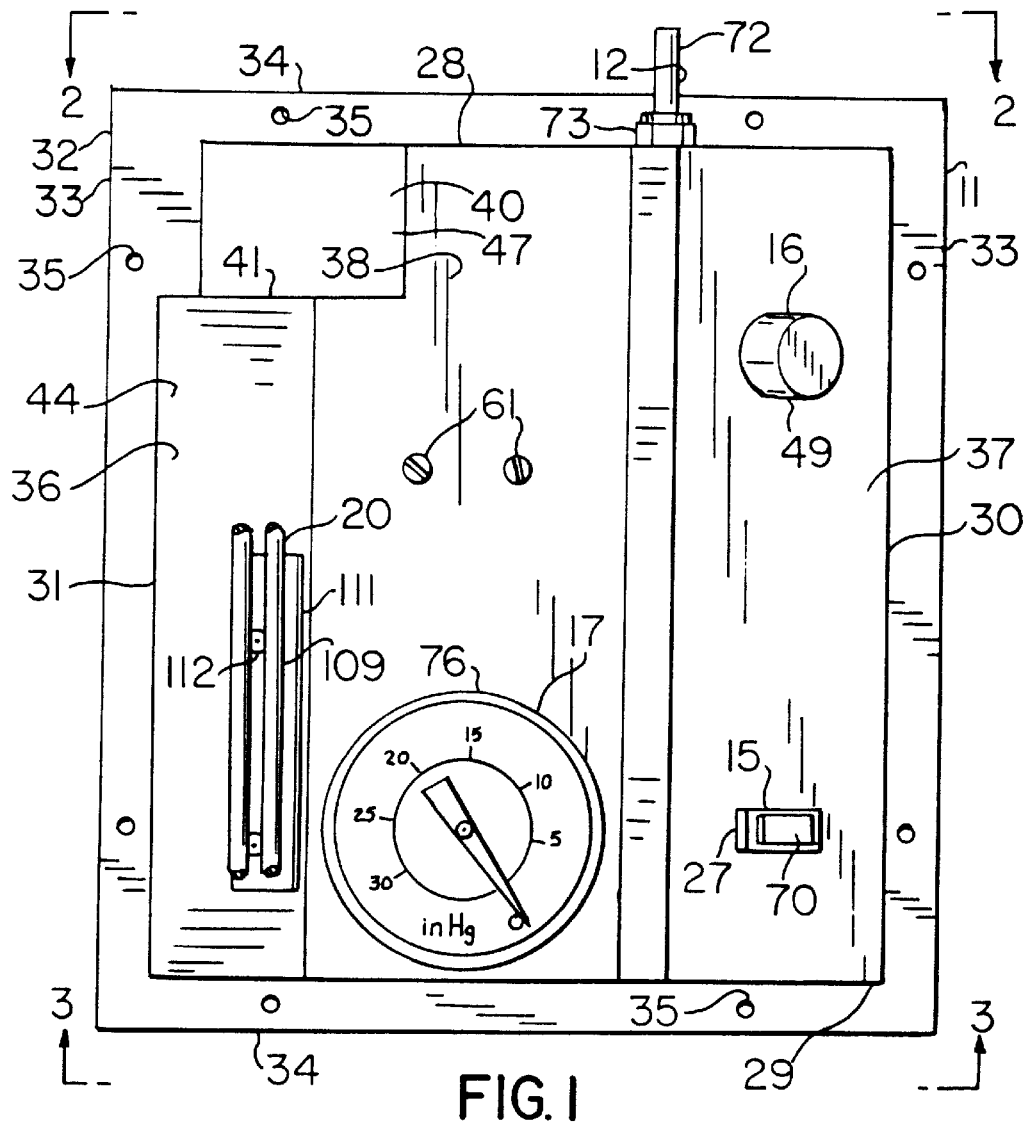

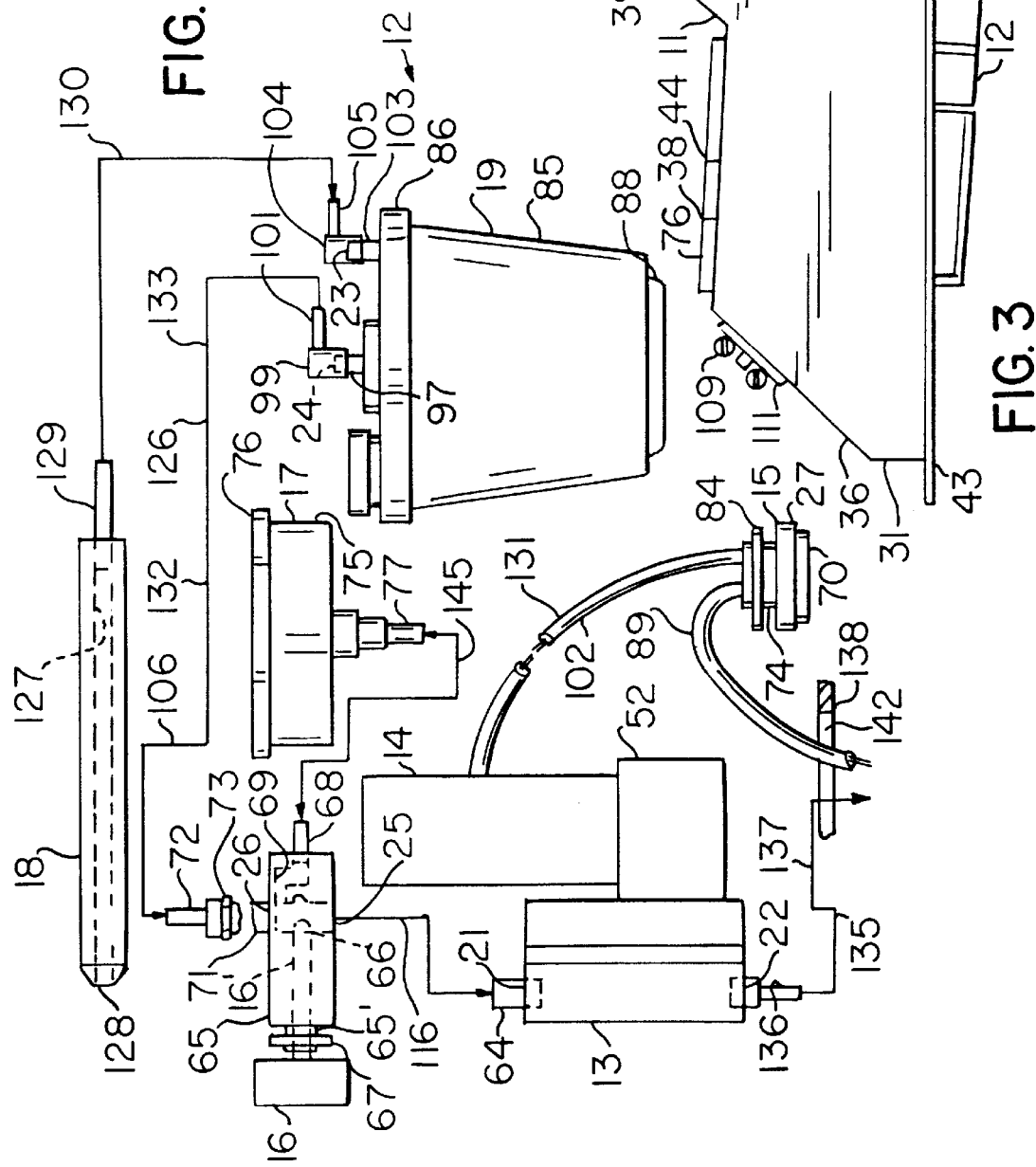

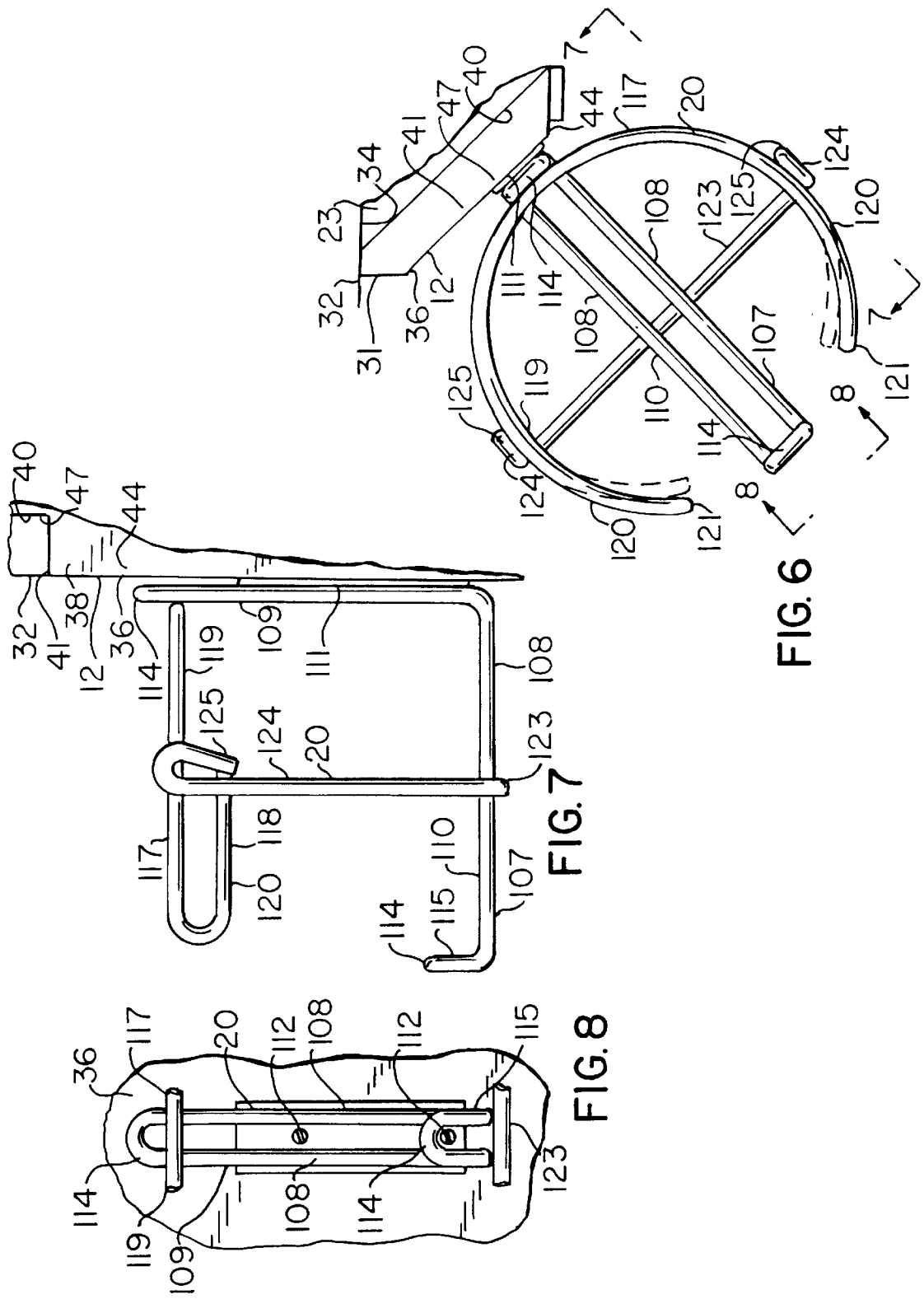

ASPIRATOR FIXTURE FOR AMBULANCES

BACKGROUND OF THE INVENTION

1. Field of the Invention (Technical Field)

The invention generally relates to aspirators which are used for removing body fluids from accident victims and other patients during their transportation to medical facilities in motorized ambulances. More particularly, the invention relates to a fixture with aspirator components and which is adapted for mounting on an internal wall in the patient transport area of an ambulance.

2. Description of the Related Art

The design of medical equipment used in treating patients that undergo transportation in an ambulance is, in many respects, limited by the electrical generating and storage facilities provided by the chassis suppliers. The standard automotive electrical system which is provided by the chassis supplier must be converted by the ambulance manufacturer to an ambulance electrical system that can handle the added load requirements imposed on the power supply under the emergency conditions encountered.

Ideally, the ambulance electrical system should be capable of handling (1) the chassis loads (i.e., the starter, ignition, basic chassis lighting, and driver cab air conditioning loads), (2) plus patient module or compartment loads (i.e., transport area lighting, air conditioning and life support loads including those for ventilators, suction units, ECG monitors, defibrillators, and infant transporters), and (3) emergency system loads (i.e., flashing, spot and other emergency lights, as well as sirens, horns and communication equipment loads).

Realistically, the load demands have in the past caused, and continue to cause, some serious difficulties. In the normal non-emergency environment, the electrical generating system (i.e., the alternator) has been adequate to handle the chassis and battery charging loads. On the other hand, in the emergency environment, the generating system has usually been found lacking in capacity. As such, battery discharge has been a common occurrence under many emergency conditions and has been known to lead to a complete battery discharge causing a cessation of operation of the ambulance motor and a consequential inability to use on-board life support units.

These electrical load demands, in the light of limitations imposed upon the ambulance manufactures by the basic electrical systems provided by the chassis supplier's, have led to a need (1) for better electrical system designs by the ambulance manufactures, (2) for better load management by those involved in the day-to-day use of the ambulances and the life support equipment and facilities provided for use by the emergency medical technicians (EMTs), and (3) for better designs of the life support equipment and facilities provided the EMTS.

Ambulance electrical system designs in the past couple of decades have centered on increasing electrical generating capacity through the use of larger and sometimes dual alternator systems, and on the use of dual maintenance—free batteries having higher cold crank and reserve capacity ratings.

Load management has improved (1) by eliminating, and reducing the use of high load consuming equipment and substituting equipment with lesser load demands, (2) by more effectively utilizing load usage indicators and protective devices, and (3) by providing better educational programs for the equipment users involved in the emergency medical services (EMS).

Life support equipment designs have also improved. Suction, ECG monitors, defibrillators, and ventilators are now commonly portable and operated by self contained power packs which involve the use of replaceable and rechargeable 12 V DC battery systems. Such packs are usually equipped with a battery charger that is designed for specific use with the unit involved, and provide for connection with a 110–115V AC power source (i.e., shore tie or on-board inverter). Use of the power packs has relieved the load demands on the ambulance electrical systems to some extent but imposed a need for 110–115V AC outlets in the patient transport area so as to provide convenient recharge power at the equipment storage point in the ambulance. The recharge power source can be from either or both a shore tie to a land based power system or through a connection with an on-board inverter. When a power pack requires recharging during transport and replaceable batteries are unavailable, the attendant must resort to the on-board inverter.

The problems associated with the presence of a high voltage AC power source in the environment of the action area of an ambulance are well known and apparent from a consideration of pages 65–71 of Report No. DOT-HS-7-01801, dated JUNE 1979, entitled "AMBULANCE ELECTRICAL SYSTEM STUDY", and prepared for the NATIONAL HIGHWAY TRAFFIC SAFETY ADMINISTRATION OF the U.S. DEPARTMENT OF TRANSPORTATION by Parker, Starmer, West and Ruddle.

As indicted therein suction equipment provides a conductive path during use which could connect the patient to an electrically active circuit. For example, suction fluids, depending on ion content, can exhibit a variety of conductivities, and thereby establish a conductive path to a patient if the fluid in the suction system gets crossed up with a shore or on-board 112-115V AC electrical source. Furthermore, blood from a wound can provide a conducting path that can connect the patient to a number of nearby conductive structures. The hazards involved in the inadvertent dumping of an aspirator canister's contents under the conditions encountered in real time emergency patient transport to a hospital facility are real.

In addition, the electrically powered devices with internal rechargeable batteries can also be inadvertently tied together through the battery charging circuitry as well as being connected to the patient. Therefore, it is important to recognize that isolation of electrically powered devices is not a most viable option for minimizing accidental electrical shock.

Although there are opportunities for both patient and attendant to receive shock in the environment of the patient transport area, it is recognized that the magnitude of the shock will be safely below that necessary to induce cardiac arhythmias provided the maximum voltage encountered is nominally 13.8 volts. Such of course is the maximum voltage available from the DC system of todays ambulances.

SUMMARY OF THE INVENTION

A general object of the invention is to provide improvements involving the use of aspirating system in ambulances.

Another object of the invention is to provide a fixture with vacuum producing components of an aspirator system and which may be mounted on a wall apart from other life support equipment in the transport area of a motorized ambulance and thereat readily connected to a catheter and used by the attendant for aspirating fluids from a patient.

Yet another object is to provide an aspirating system of improved safety which is less likely to be involved in an encounter with high voltage using equipment in the transport area and thereby less likely to establish a conductive path for imparting a hazardous shock to a patient or attendant.

Still another object is to provide a fixture which contains vacuum producing components that are compactly housed for mounting on an internal wall in the patient transport area of an ambulance.

One particular object is to provide a fixture with a housing for supporting permanently emplaced components of an aspirator system and which includes a bracket for supporting many of the differently dimensioned canisters that are in common use with suction equipment found in ambulance environments.

Another object is in accord with the prior object and is further concerned with improvements in the structure of brackets for supporting such canisters.

Yet another objective is to provide a fixture with a multipanel housing which provides a cavity area for compactly housing components of an aspirator system, is adapted for mounting on an internal wall in the patient transport area of an ambulance, and has a panel arrangement that is conducive to mounting a canister support bracket in a manner such that the canister is located in close proximity to the wall and thus away from other life support devices in the transport area.

Another objective contemplates the preceding objective with a further objective of providing a panel arrangement for supporting vacuum producing, control and monitoring components in a transport area location where such components are readily accessible and/or viewable by the attendant.

The invention contemplates a fixture housing that is mountable on an interior wall of the transport area of an ambulance. It has a multipanel structure that provides a cavity behind the panels and which provides a place to mount components of an aspirator system in a compact arrangement both within the housing cavity and at the front side of the housing.

Vacuum producing components of an aspirator system, including a diaphragm pump and a vacuum condition control valve are mounted in the cavity, and in accord with certain aspects of the invention, the gas intake of the pump and the gas outlet of the valve are aligned and arranged in close proximity to facilitate a compact housing arrangement. Other aspects of the invention, contemplate a valve arrangement in which an element of the valve is located at the exterior of one of the panels and thereat manipulatable to control the vacuum conditions in the aspirator system.

Yet another aspect has to do with mounting a drive motor for the pump in the cavity and its connection with the 12 V DC power supply through an electrical switch which is mounted on a panel of a housing for the motor and is manipulatable to energize and de-energize the motor, the connection with the ambulance electrical system being one that avoids the presence of wiring in the transport area. Yet another aspect has to do with the display at another panel of the housing of the vacuum condition provided by operating the pump at the setting of the valve.

The housing has a rear opening into the cavity and in accord with certain aspects of the invention the interior wall has a aperture which confronts the opening and provides an accessway between the cavity and a space between the interior wall and an outer wall of the ambulance. This arrangement is provided to facilitate an electrical connection with the 12V DC power supply of the ambulance electrical system via a connecting lead that extends through the accessway and the space between the walls. The accessway also permits a conduit connection between the fluid discharge of the pump and the exterior of the ambulance and all without encounter with high voltage AC electrical system components commonly present in the transport area.

DESCRIPTION OF THE DRAWINGS

The novel features which are believed to be characteristic of this invention are set forth with particularity in the appended claims. The invention, itself, however, both as to its organization and method of operation, together with further objects and advantages thereof, may best be understood by reference to the following description taken in connection with the accompanying drawings, where:

FIG. 1 is a front elevational view of a fixture forming a preferred embodiment of the invention, certain parts being removed and others broken away;

FIG. 2 is a top plan view of the fixture shown in FIG. 1 as seen along the lines 2—2 therein, certain parts being illustrated in phantom and/or removed, and others being broken away;

FIG. 3 is a bottom plan view of the fixture shown in FIG. 1 as seen along the lines 3—3 therein, certain parts being removed and/or broken away;

FIG. 6 is a top plan view of a canister support bracket component of the fixture shown in FIG. 1 together with adjacent structure of the fixture to which the bracket is secured, certain parts being removed and others broken away;

FIG. 7 is an elevational view at one side of the support bracket component shown in FIG. 6 together with adjacent structure of the fixture secured thereto, certain parts being removed and others broken away, all as generally seen along the lines 7—7 in FIG. 6;

FIG. 8 is an elevational view at the front side of the support bracket component shown in FIG. 6 together with adjacent structure of the fixture secured thereto, certain part being removed and others broken away, all as generally seen along the lines 8—8 in FIG. 6;

FIG. 11 is a schematic illustration which primarily shows the electrical and air conduit connections involved in the aspirator system provided when the fixture is installed in a motorized ambulance,

DESCRIPTION OF THE PREFERRED EMBODIMENT

Figure 5:
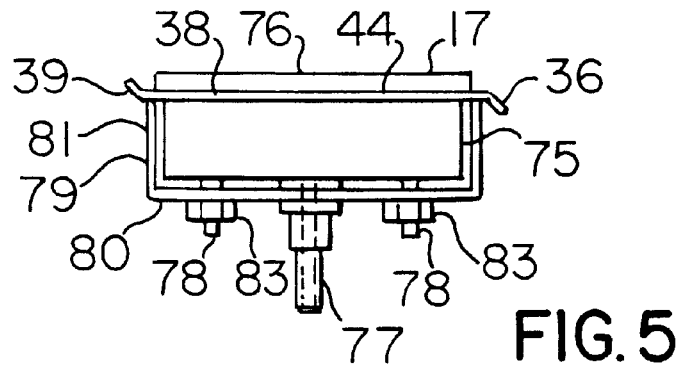
FIG. 5 is a top view of a fragment of the fixture shown in FIG. 1 and as generally seen along the lines 5—5 in FIG. 4, certain parts being removed and others broken away.

Reference is now made to the embodiment shown in the drawings and wherein a fixture embodying principles of the invention is designated at 10. Fixture 10 is adapted for attachment to an internal wall of a motorized ambulance so as to thereat provide permanently emplaced components of an aspirator. It includes a housing 11 and components of an aspirator 12. The housing 11 provides a support and mounting place for certain of the aspirator components and the aspirator 12 is used for collecting body fluids that may be secreted by a patient being transported by the ambulance.

The aspirator components mounted on the housing 11 include a diaphragm pump 13 (FIGS. 2–4, 10) which is operable to provide a vacuum condition suitable for the aspiration procedures involved, a DC motor 14 (FIGS. 2, 4, 10) for driving the pump 13, and a suitable switch 15 (FIGS. 1, 3, 4, 10) that is manipulatable to electrically connect and disconnecting the motor 14 to the 12 V DC electrical power supply of an ambulance when the fixture 10 is operatively mounted, for example, in the patient transport or action area thereof.

The aspirator 12 also includes a valve component 16 (FIGS. 1–4, 10) which is mounted in the housing 11 and used in manually regulating the vacuum condition being provided by the aspirator. As will be seen, the gas outlet 25 of the valve 16 communicates with the gas intake port 21 of the diaphragm pump 13 while the gas inlet 26 (FIG. 2) of the valve 16 communicates at the exterior of the housing 11 with the fluid outlet 24 of a canister 19 (FIGS. 9, 10) when the aspirator 12 is fully assembled and in use. The aspirator 12 also includes a pressure gauge component 17 (FIGS. 1–4, 10) which is mounted on the housing and connects with the control valve 16. At the front of the fixture, the gauge provides a visual display of the controlled vacuum condition being provided by the vacuum producing system.

The aspirator 12 in the preferred embodiment illustrated, also includes a suitable hand manipulatable suction catheter or cannula 18 which is connected via a flexible plastic tube, during use, to the fluid intake of the canister 19 (FIG. 11). The catheter 18, during use, is inserted by the attendant in a body cavity of a patient to aspirate fluids therefrom. In some cases, the attendants avoid use of a preformed catheter and aspirate fluids from a body cavity by simply inserting the free end of a flexible plastic tube in the cavity and which at its other end is connected to the fluid intake of the canister 19.

The canister 19 itself is supported by a bracket 20 (FIGS. 1–3, 6–8) that is located at the exterior of the housing 11 and where it is mounted at the front side 44 of the housing 11. The canister 19 serves as a receptacle for collecting fluids aspirated from a patient when the aspirator is being used and, as indicated, the fluid inlet 23 (FIG. 9) of the canister 19 communicates, in the preferred embodiment, with the catheter 18 during use of the aspirator system.

The fluid or suction outlet 24 (FIG. 9) of the canister 19, on the other hand, is normally connected to the gas inlet 26 of the needle valve 16 and, in use, is under a vacuum condition that is controlled by the attendant's operation of the needle valve 16. The arrangement overall is such as to establish a vacumn condition at the catheter 18 for sucking up fluids from a patient being transported in the vehicle and delivering such fluids to the canister 19 for retention of the liquids thereby.

Housing 11 is preferably a one piece preformed and configured structure that is suitable for supporting the vacuum producing and controlling components of the fixture and for use in compactly mounting and retaining such components in the work or action area of an ambulance. The housing 11 may be stamped from suitable metallic sheet material, but is preferably fabricated or molded through the use of fiberglass and suitable resinous materials, such as an epoxy resin, although other assembly and fabrication procedures utilizing other appropriate materials may be used for providing the above mentioned mount and support functions.

Housing 11 has a flat, suitably configured, and horizontally arranged top panel 28 (FIGS. 1, 2, 4 and 6) that is located at the upper end of the housing. It also has a flat, normally horizontally arranged and suitably configured bottom panel 29 (FIGS. 1 and 3) that is located at the lower end of the housing 11.

Panels 28 and 29 are vertically spaced apart and, at the right side of the housing 11, are respectively joined to the upper and lowers ends of a narrow, flat, rectangular and vertically arranged side panel 30 (FIGS. 1–3) of the housing 11. At the left side of the housing 11 is another narrow, flat, rectangular and vertically arranged side panel 31 (FIGS. 1–3 and 6). This panel 31 is joined at its lower end to the bottom panel 29 and is generally arranged in parallel with the right side panel 30.

The top and bottom panels 28 and 29 and the opposite side panels 30 and 31 are joined to a laterally outwardly extending peripheral flange component 32 (FIGS. 1–4, 6, 7, 10) of the housing 11. The opposite side sections 33 of the flange and the opposite end sections 34 of the flange 32 at the upper and lower ends of the housing 11 are integrally joined in a common plane. All of these sections 33 and 34 are equipped with spaced holes 35 (FIG. 1) which will be seen in the consideration of FIG. 10 to accommodate suitable fasteners that are used in securing the housing 11 to the internal wall of an ambulance. As joined to the flange 32, each of the panels 28, 29, 30 and 31 is arranged in a respective plane that is perpendicular to that of the flange 32.

In addition to the opposite side panels 30 and 31 and the opposite end panels 28 and 29, the housing 11 has vertically oriented flat front panels 36, 37, 38, 39, and 40 (FIGS. 1–4, 10) which are generally located at the front of the housing 11. Panels 36, 37, 38, and 39 are offset outwardly of the plane of the flange 32. Panel 40, on the other hand, joins the flange 32 along its left side and, inwardly thereof in the housing structure, is generally outwardly offset from the plane of the flange 32 and in parallel with the lower left front panel 36.

At its upper end the left front panel 36 is joined to another configured horizontal panel 41 (FIG. 1, 2, 4 and 10) that is, in turn, joined to the lower extremity of panel 40 in the formation of a frontal recess 47 that will be considered below. All of these panels are joined together and cooperate in defining an internal housing cavity 42 for locating certain components of the aspirator 12. This cavity 42 opens to the housing exterior at the back or rear side 43 of the housing 11 and the opening 45 (FIG. 4) is defined by the inner edge 46 (FIG. 4) of the peripheral flange 32.

The bracket 20 for the canister 19 is mounted on the lower left front panel 36 of the housing 11. At the front side 44 of the housing 11, this flat panel 36 is arranged at an obtuse angle to the plane of the flange 32 so that when the canister 19 is supported by the bracket 20, it occupies a position in the transport area which is in close proximity to the wall and thus out-of-the-way of the attendant's arm movement range for patient monitoring and treating the patients conditions.

Figure 10:
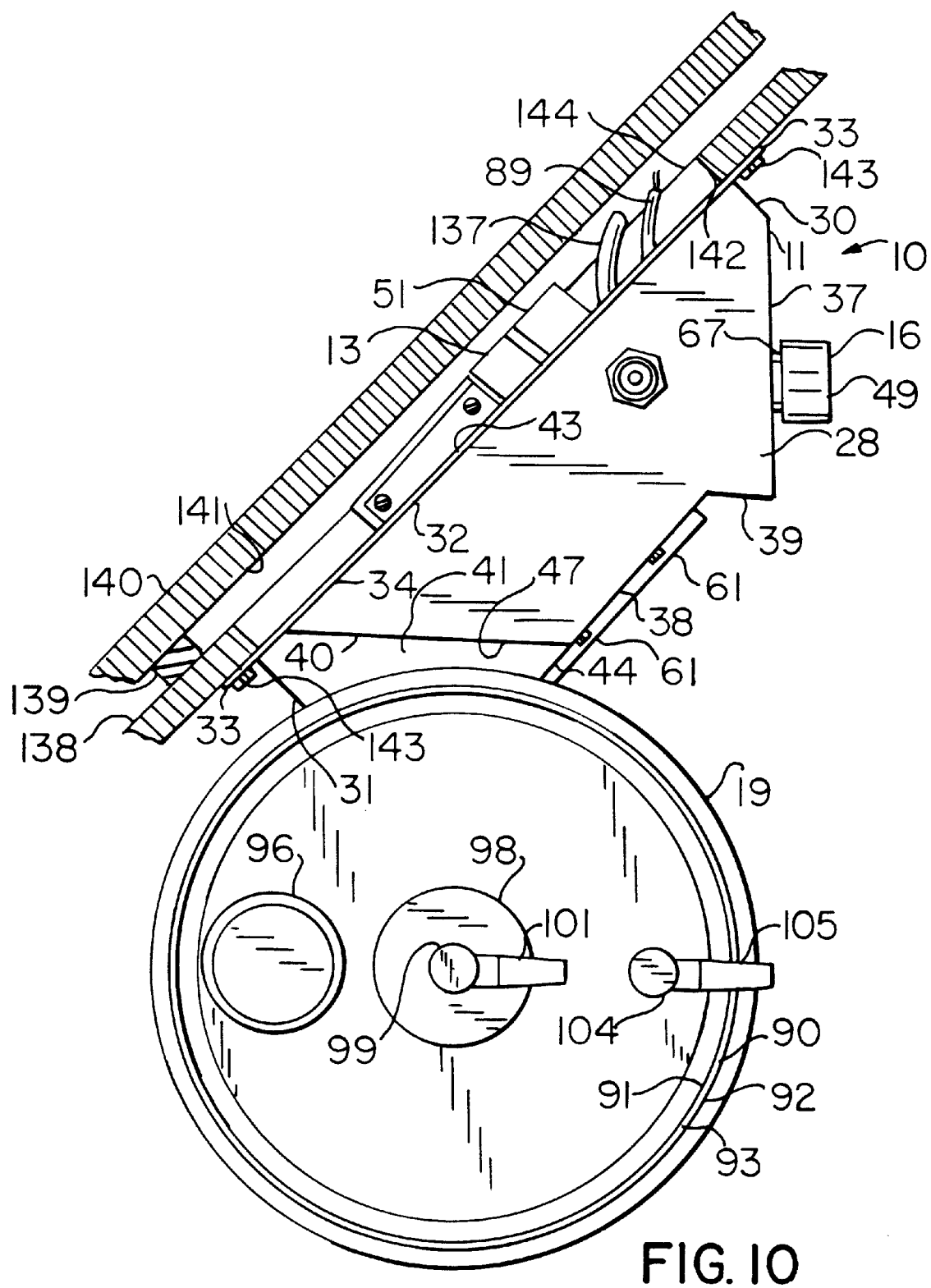
FIG. 10 is a top plan view of the fixture illustrated in FIGS. 1–9 as seen, in relation to an exterior wall and interior wall of an ambulance, and when mounted on the interior wall in the patient transport area of a motorized ambulance, certain parts being removed and other parts broken away.

The upper end of panel 36 is joined to the intermediate horizontal panel 41 and the latter is, in turn, joined to the bottom end of the upper left front panel 40. Front panels 36 and 40 are in a parallel arrangement with the latter being offset rearwardly from the plane of panel 36. This arrangement, as indicated above, provides a frontal recess 47 in the housing 11 at the upper end of panel 36. As such, when the canister 19 is seated on the bracket 20, the recess 47 accommodates the laterally flaring nature of the canister structure at the upper or lid end thereof (FIG. 10).

Overall, the arrangement of the bracket 20 on the angularly arranged panel 36 with the housing recess 47 thereabove serves to provide a compact fixture structure not only for housing the vacumn producing components of the aspirator 12 but also, when the housing 11 is mounted on a wall, for supporting the body fluid storing canister 19 in an area which is out-of-the-way of the attendant's principal arm movement area for monitoring and treating a patient undergoing transport. As will also be seen, when the fixture 10 is properly mounted in the transport area of an ambulance, the vacuum producing functions of the aspirator 12 are carried out and monitored by components that are readily accessible for control and/or view by the attendant but nevertheless out-of-the-way of the main arm movement areas for treating the patient in the action area of the ambulance.

The center front panel 38 serves as a structural support for mounting the pump 13 and drive motor 14 in the cavity 42 and also as a convenient place to mount the pressure gauge 17 in a frontal area of the housing and at which it can be readily viewed by the attendant. At its opposite sides, the flat center panel 38 is joined to panels 36 and 39. At its upper and lower ends, the center panel 38 is joined to the horizontal top and bottom panels 28 and 29 respectively.

The right front panel 37 has a rectangular configuration and at the front side 44 of the housing is arranged at an obtuse angle to the plane of the flange 32. This angular arrangement again facilitates a compact mounting arrangement in the cavity 42 for the pump 13 and valve 16 and whereat, it will be seen that connection of the pump and valve is facilitated by an aligned arrangement in close proximity of the gas intake port 21 for the pump 13 and the gas outlet 25 of the valve 16. This panel 37 arrangement also facilitates the location in a readily accessible exterior area on the housing 11 of a rotatably manipulatable knob component 49 of the valve 16 so as to facilitate manipulation and control of the valve 16 at the front of the fixture 10 by the attendant. The arrangement also facilitates the mounting of the switch 15 for energizing and deenergizing the motor 14 at a convenient location for manipulation by the attendant.

Panel 39 is a narrow structure joined at its opposite sides to front panels 38 and 37 while at its upper and lower ends, the elongated panel 39 is joined to the top and bottom panels 28 and 29 of the housing 11. It serves in the overall housing structure to support and maintain the angular arrangement of the side and front panels 37 and 38 involved in the housing structure.

Reference is now made to FIGS. 1–4 to illustrate the mounting arrangement for the diaphragm pump 13 and DC motor 1 in the cavity 42 and the means utilized for securing these aspirator components to the fixture housing 11.

Experience has shown that piston and rotary vane pumps are less suited for mounting in a compact arrangement with suitable valving devices in an ambulance environment than diaphragm pumps. As such, a diaphragm pump is contemplated for use as a vacuum producing component of the fixture in accord with the invention. The specific structure of the diaphragm pump forms no part of the invention. However, it should be capable in use under the transport conditions encountered of continuously pumping at least 30 liters of air per minute and provide a vacumn condition of at least 500 mm of Hg at the patient end of the suction tube 130 (FIG. 11).

The diaphragm pump 13 illustrated in the drawings has a diaphragm section 51 and a motion translation section 52. The former section 51 has the gas intake port 21 and the gas discharge or outlet port 22 previously mentioned. It is also equipped with a suitable diaphragm (not shown) as well as an intake and outlet valve systems (not shown) for, in sequence and alternately, opening and closing the ports 21 and 22 as the diaphragm is subjected to a reciprocating motion that is imparted to it by components of the motion translation section 52.

Section 52 may comprise a simple crank (not shown) that is attached to a shaft which is rotatably driven by motor 14 and wherein the crank and diaphragm are suitably interconnected by an arm (not shown) to impart linear motion to the diaphragm in a manner well known in the art.

Figure 4:
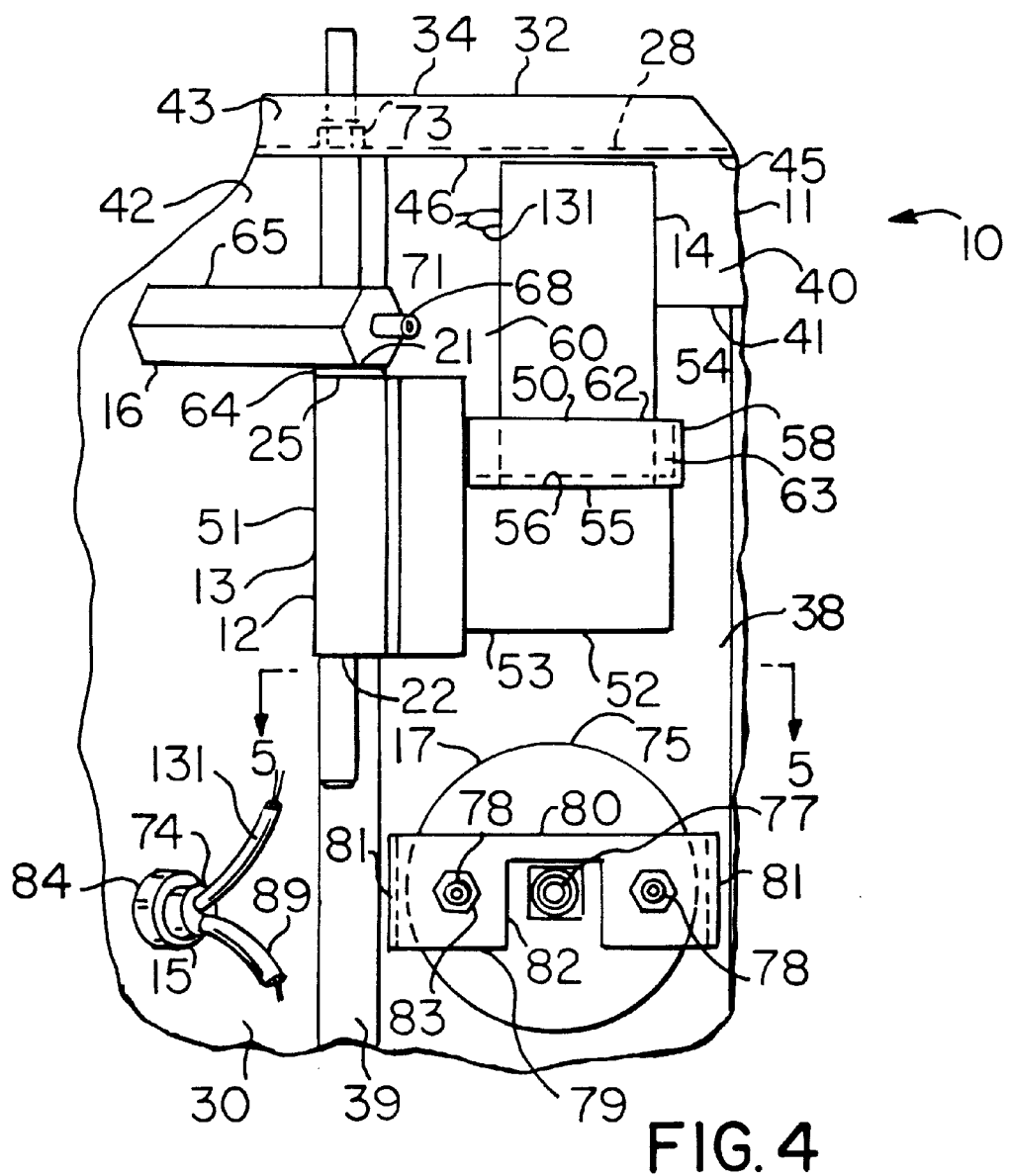
FIG. 4 is a rear elevational view of a fragment of the fixture shown in FIG. 1 and as generally seen along the lines 4—4 in FIG. 2, certain parts being removed and others broken away.

The assembled diaphragm section 51 is fixed to the housing 53 for the translator section 52 and the cylindrical motor housing 54 is, in turn, fixed to the translator housing 53 as seen in FIGS. 2 and 4. The assembled motor 14 and pump sections 51 and 52 are mounted and supported on the center front panel 38 by means of a bracket designated at 50. Bracket 50 has a flat rectangular plate component 55 and an upstanding flange component 58. The latter component 58 has three side sections 59, 62 and 63 that extend along, and are integrally joined to, respective side edges of the rectangular plate structure 55.

The flat plate 55 is arranged perpendicular to the longitudinal axis of the motor 14 in the assembled fixture 10 and is securely fixed to, and over, the upper side face 56 of the translator housing 53 by means of suitable fasteners 57 (FIG. 2). The plate 55 has a circular opening which accommodates the location of the motor 14 and enables the plate 55 to facially confront the housing side face 56 in the assembled structure.

The front section 59 of the flange 58 facially confronts the interior or cavity side 60 of the center front panel 38. Here, the pump and motor supporting bracket 50 is fixed to the panel 59 by means of a pair of threaded fasteners 61 (FIG. 2). These fasteners 61 are spaced apart and each has a threaded element that extends through aligned holes in the front panel 38 and abutting flange section 59. At the cavity side 60 of the housing, these threaded elements are threadedly engaged by suitable nuts that serves to clamp the panel 38 and flange section 59 together and thus securely fasten the vacuum producing components to the housing 11. The back section 62 and the interconnecting section 63 which integrally joins the front and back sections 59 and 62 of the flange 58 serve to stabilize the mounting and add rigidity to the bracket structure 50.

The valve 16 is rigidly connected to the pump 13 in the cavity 42 by a small nipple 64 (FIG. 4) which is threaded at its opposite ends and threadedly engages the pump 13 and valve 16 in the pump intake port 21 and valve outlet 25 respectively. Here, the nipple 64 serves as a coupling for the passage of gas from the needle valve 16 to the pump 13. The coupling to the pump 13 is made at the inner end of the elongated valve housing 65. The valve housing 65 is so oriented with respect to the pump 13 that the outer end of the housing 65 bears against the interior or cavity side 60 of the right front panel 37. At its outer end, the valve housing 65 is equipped with a neck piece 65' that extends through an aperture (not shown) in the panel 37 and whereat it is threadedly engaged at the exterior of the housing 11 by a collar 67 (FIG.11). This arrangement serves to clamp the panel 37 between the collar 67 and outer end of the housing 65.

At the exterior of the housing, the valve 16 is provided with a knob 49 which is secured to a conventional needle shaft 16'. This shaft extends through the collar 67 and neck piece 65' of the assembled valve 16 and is threaded in the housing 65 for controlled axial movements to obstruct the gas passageway 66 (FIG. 11) between the valve inlet 26 and outlet 25. The amount of gas drawn into the pump intake port 21 is thus regulated by rotative manipulation of the knob 49.

At its inner end extremity, the valve housing 65 has another passageway 69 that communicates with the transverse passageway 66 and at the air inlet end thereof. The passageway 69 is equipped with a tubular fitting 68 that facilitates a connection, via a plastic tube length 145 (FIG. 11), with the vacumn gauge used in monitoring the pressure in the aspirator system. With this arrangement, the gauge provides a continuing visual readout of the vacuum condition prevailing at the upstream side of the valve.

The switch 15 is also mounted on panel 37. In this case, the switch 15 is mounted below the manipulatable knob 49 for the needle valve 16, as best seen in FIGS. 1 and 4. The switch 15 has a button housing 27 which is located at the exterior of the housing 11 and where it is mounted on the right front panel 37. Here, the housing 27 is equipped with a button 70 that is manually operable by the attendant and manipulated by successive depressions to make and break the electrical circuit which energizes and deenergizes the motor 14. Switch 15 is a typical double-pole, double-throw switch and the housing 27 has a neck piece 74 that extends into the cavity 42 through a suitable opening in the panel 37. At the interior or cavity side 60 of the panel 37, the neck piece 74 is threadedly engaged by a collar 84 which bears against the panel 37 and firmly retains the switch housing 27 in place at the front side 44 of the panel. In the cavity 42, the switch 15 is connected to a two-wire lead 89 that connects the switch 15 to the 12 V DC power system of the ambulance. As will be seen, when the fixture 10 is appropriately mounted on the internal wall of an ambulance, this lead 89 extends through the accessway to the space between the internal and exterior walls to the ambulance DC power system. As such, the lead 89 is isolated from all high voltage power systems in the patient transport area of the ambulance. In the cavity 42, the switch 15 is also connected to another two-wire lead 102 and which connects the switch to the DC motor 14. This lead is wholly contained in the cavity 42 and thus away from all on-board high voltage systems.

The location of the switch button 70, being on the same panel 37 as the knob 49, places the switch 15 in a convenient location for manipulation by the attendant, yet in an out-of-the way area of continuous hand movement by the attendant in treating a patient under transport.

Access to the valve inlet 26 for establishing a connection with the canister 19 is gained at the upper end of the housing 11. A hole (not shown) in the top panel 28 is provided to accommodate a vertically arranged conduit 71 which extends through the hole and, at its lower end, is threaded into the valve inlet 26. At the exterior of the housing 11, the upper end of the conduit 71 is threadedly engaged by a nut 73 which bears against the exterior face of the panel 28 and aids in fixing the mounted location of the pump and valve in the cavity. The nut 73 is integrally joined to an upright extending sleeve 72 which communicates with the conduit 71 and provides a fitting at the exterior of the housing for coupling the valve 16 and canister 19 together.

At its lower end, the center front panel 38 has a circular opening (not shown) into the cavity 42 and which is adapted to receive a cylindrical body part 75 of the vacumn gauge 17. The gauge 17 has a flange 76 at its viewing end and the flange 76 extends radially of the opening and bears against the front side 44 of the panel 38 when the body part 75 is received in the panel opening and secured in place.

The body part 75 of the gauge 17 has a rearwardly extending tube 77 which threadedly engages the body part 75 in an axially located air passage that communicates with the interior of the gauge 17. The tube 77 serves as a fitting for a flexible plastic tube 145 connection with the fitting 68 of the needle valve 16. The body part 75 also has a pair of threaded elements 78 that extends rearwardly in the gauge and which are diametrically offset from the tube 77.

The method of mounting the gauge 17 on the center panel is best seen in FIGS. 4 and 5. The gauge 17 is held in place by a U-shaped bracket 79. The bracket 79 has a center portion 80 which is rearwardly offset from the body part 75 and extends transversely thereof at the inner end of the gauge 17. The bracket 79 also has a pair of forwardly extending legs 81 that, at the opposite sides of the body part 75 are located in close proximity thereto. The center portion 80 has a cutout 82 which accommodates the location of the tubular fitting 77, and also has a pair of holes (not shown) which respectively receive and are aligned with the threaded elements 78. The legs 81 bear against the cavity side 60 of the panel 38 and in close proximity to the cylindrical body part 75. In the final assembly of the fixture, the elements 78 are threadedly engaged by a pair of nuts 83 which serve to draw the flange 76 into secure facial contact with the exterior side 44 of the panel 38.

The canister is supported on a bracket 20 which is mounted at the exterior side 44 of the lower left front panel 36. It provides a reservoir for the collection of body fluids that are aspirated from a patient. A typical canister 19 that may be used as a component of the aspirator 12 is best seen in FIG. 9.

The assembled canister 19 includes a jar 85 which serves as the reservoir in which the body fluids are collected during use of the aspirator 12. The canister 19 also has a cover or lid 86 which is structured to cooperate with a narrow upright cylindrical rim 87, located at the mouth of the jar 85, to provide an airtight seal between the jar 85 and lid 86. The jar 85 may be formed in any suitable way and from any suitable material. Typically the jars used in conventional aspirators are molded of plastic material and may be made from , a polysulfone, polycarbonate or polystyrene among other materials. The structure of the illustrated jar 85 is such that, in general, the diametric dimension progressively increases upwardly from the bottom 88 of the structure to its cylindrical rim 87, as is evident in FIG. 9.

The lid 86 may also be formed in any suitable way and from any suitable material. Typically, the lids used in conventional aspirators are molded of a softer, more pliable plastic material than conventionally used in forming the jars and among such materials may be mentioned the polystyrenes, polycarbonates and butyrates.

Figure 9:
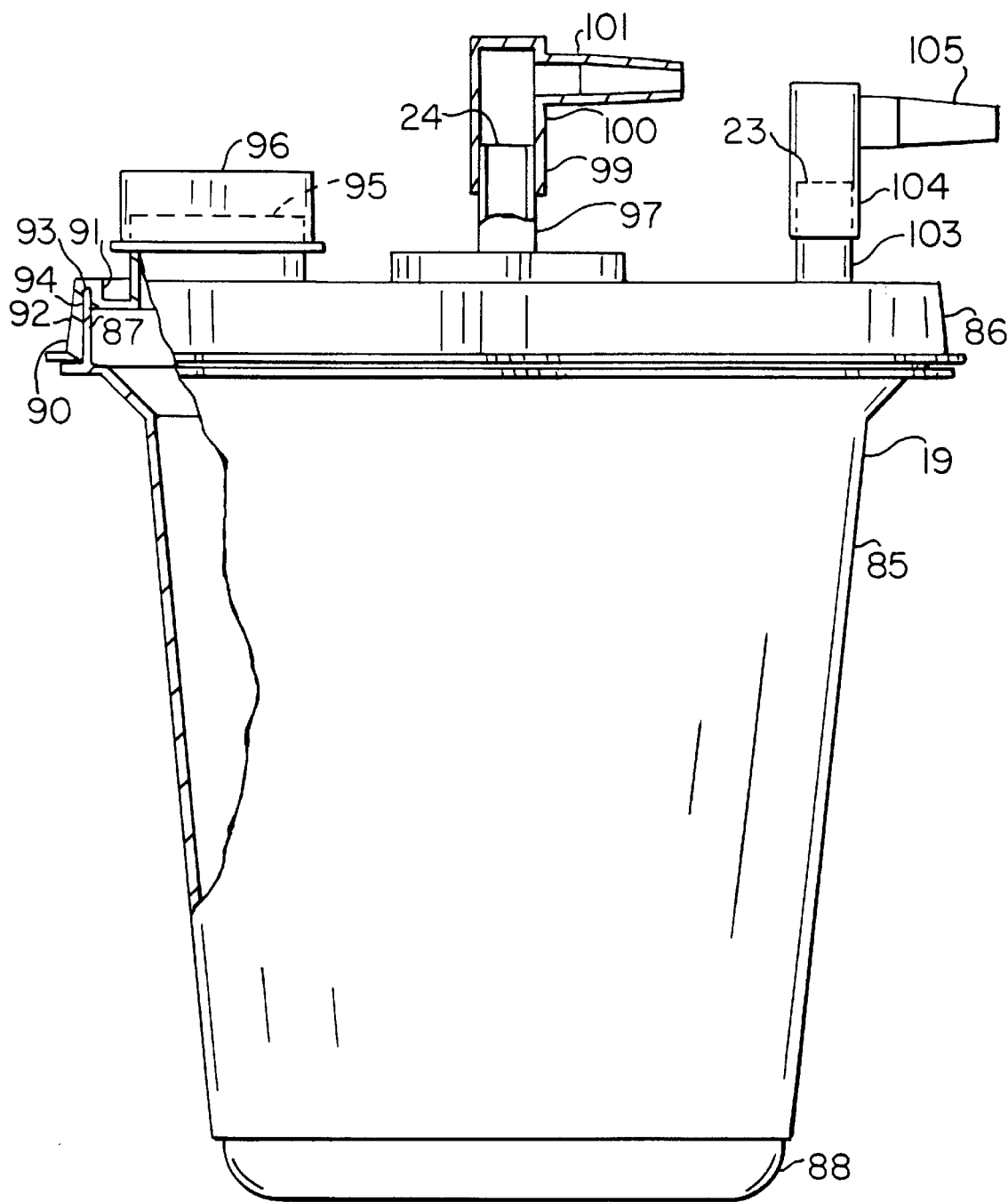
FIG. 9 is an enlarged side elevational view of an assembled canister that may be used with the system provided by the fixture, certain parts being broken away to show the structure of certain other parts of the canister.

Structurally, the lid 86 illustrated in FIG. 9 has a generally circular perimeter section 90 which includes radially spaced apart inner and outer portions 91 and 92, and a ridge portion 93 that interconnects the inner and outer portions and overlies the rim 87 of the jar 85 in the assembled canister 19. The outer portion 92 of the perimeter section 90 surrounds the cylindrical rim 87 of the jar 85 and is abuttingly contiguous with the outer wall of the rim 87 in the assembled canister 19. The inner portion 91, on the other hand, is contiguous with the inner wall of the rim 87 in the proximity of the mouth of the jar 85 when the canister is fully assembled. The ridge portion 93 of the section 90 integrally joins the inner and outer portions 91 and 92 and therewith forms a cylindrical slot 94 in which the rim 87 is received to form an airtight seal at the mouth of the jar when the canister 19 components are assembled.

The lid 86 structure inwardly of the rim section 90 provides the assembled canister 19 with a fluid inlet 23, a fluid outlet 24, and a cylindrical pour spout 95. The spout 95 is normally closed by a removable cap 96 that is adapted to fit thereon and thereat hermetically seal the canister. The spout 95 is useful, during emergency situations, in dumping the jar contents without removing the lid 86 from the jar 85.

The fluid outlet 24 is formed by an upright hollow conduit 97 which is an integrally formed part of the lid 86 and communicates with the reservoir area in the jar 85 through a conventional float type valve (not shown) that closes the fluid outlet 24 when the jar is full. The float type valve is housed in a cylindrical section 98 of the lid 86 and which is located centrally in the lid structure. The outlet forming conduit 97 communicates with the interior of the canister 19 through this valve section 98. An adapter 99 is provided for the outlet forming conduit 97 so as to facilitate connecting the fluid outlet 24 to the end of a plastic tubular component which communicates with the diaphragm pump 13 during use of the aspirator 12. The adapter 99 is of convention construction and has a cylindrical conduit section 100 that is closed at its upper end. At the lower end, the section 100 is open and snugly fits on the outlet conduit 97 to therewith, at the upper end of the conduit 97, provide a fluid seal between the parts. The conduit section 100 also has a radially extending tapered conduit section 101 that is designed for reception in the end of a plastic tube which interconnects the canister outlet with the exterior tube fitting 72 on the fixture 10. The tapered section 101 is integrally joined with section 100 in the molding of the adapter 99. This section 101 is mounted on, and communicates with, the upright section 100 of the adapter 99 as seen in FIG. 9.

The fluid inlet 23 is formed by another upright hollow conduit 103 which is an integrally formed part of the lid 86 and communicates with the reservoir area of the jar 85. This conduit 103 is also equipped with an adapter 104 which is structurally like that of adapter 99. The tapered conduit section 105 of the adapter 104 facilitates a plastic tubular connection 130 (FIG. 11) between the canister fluid inlet 23 and the end fitting 129 on the catheter 18 of the aspirator 12.

The structure of the canister supporting bracket 20 is best seen and understood by a consideration of FIGS. 1–3 and 6–8. The bracket 20 is mounted on the lower left front panel 36 and is adapted to retain the canister 19 in front of this panel 36 and in close proximity to the ambulance wall when the fixture 10 is appropriately mounted thereon. The bracket 20 includes three sections which are respectively made from wire lengths that are welded or otherwise appropriately joined together in the assembled structure of the bracket 20. The wire lengths are of a suitable gauge that enables the bracket to support a full, fluid containing canister 19 and to restrict its lateral movements under the normal conditions involved in transporting a patient.

The main support section 107 for the canister 19 is made from a first wire length in which the opposite end extremities of the length are arranged to abut and thereat suitably joined, for example, by welding. The endless length is bent to provide a narrow canister support section 107 with a pair of elongated and closely spaced wire components 108 that are integrally interconnected at their opposite ends by arcuate end components 114. The spaced wire components 108 are also bent to provide an upright back portion 109 and a horizontally arranged bottom portion 110 in the main support section 107 of the assembled bracket 20. At the outer end of the bottom portion 110, the spaced wire components 108 are also bent to provide a shirt upright end part 115 at the front of the support section 107 and which aids in restricting canister movements thereat.

The upright back portion 109 is welded to a narrow upright mounting plate 111 that is arranged contiguous to the exterior side 44 of the lower left front panel 36. This plate 111 and the attached bracket 20 are secured at the front of -he panel 36 by a pair of fasteners 112 (FIG. 2) which extend through appropriately aligned holes in the front plate 111 and panel 36 and then through holes aligned therewith in another upright and flat plate 113 (FIG. 2) that is located in the cavity 42 and at the cavity side 60 of the panel 36. In the cavity 42, the fasteners 112 are threadedly engaged by suitable nut elements (FIG. 2) which are used in clamping the panel 36 between the outer and inner plates 111 and 113 in the assembled fixture 10.

A second wire length is used to provide another bracket section 117 which is designed to embrace the side walls of a canister being supported thereon so as to restrict the lateral movement thereof and thus retain the canister on the support section 107. This second length has a horizontally arranged intermediate arcuate portion 119 (FIG. 6) and opposite end portions 118. Each of the end portions 118 is bent downwardly about a return bend and then backwardly to, in parallel, underlie and, in the proximity of the intermediate portion 119, follow the arcuate contour of the overlying arcuate portion 119 (FIG. 7).

The intermediate arcuate portion 119 of the section 1.17 is arranged horizontally and spacedly above the horizontal bottom portion 110 of the main support section 107. Midway between the return bends, the intermediate portion 119 of section 117 is welded to the upright back portion 109 of the support section 107. This arrangement provides a pair of horizontally spaced apart arms 120 which are located above the bottom portion 109. A canister supported on the bottom portion is located between, and thus embraced by, the arms 120 and is thus restricted in its lateral movements on the bracket 20.

The arrangement of sections 107 and 117 is reinforced by a third wire length that is bent and shaped to interconnect the sections at points offset from the back portion 109 of the support section 107. This serves to maintain the spaced relationship of the sections 107 and 117 and provides a reinforcing section 122 in the bracket structure.

This third length of wire is bent to provide parallel opposite end portions 124 that are integrally joined to and arranged perpendicular to an intermediate portion 123 of the length. In the assembled bracket 20, the intermediate portion 123 underlies and extends transversely of the narrow bottom portion 110 of section 107. Here, the intermediate portion 123 is welded or otherwise securely joined to the narrow bottom portion 110 of the support section 107 and the opposite end portions 124 are arranged upright at the opposite sides of the bracket 20. At the upper end of each side forming component 124, the wire length is provided with a return bend 125 that is welded or otherwise securely joined to the intermediate portion 119 and the adjacent end portion 118 of the wire length 118 forming the retainer section 117. As seen in FIG. 6, the distal end portions 121 of the arms 120 are horizontally offset. However, they may be deformed and bent to embrace and restrict lateral movements of canisters having a different transverse dimensional size than that shown in the drawings as indicated by the bent positions shown in FIG. 6.

The route traversed by the fluids entering the circuit 126 during the operation of the aspirator 12 is best illustrated by reference to FIG. 11.

The catheter 18 may take on any form suitable for manipulation by the attendant and which may be conveniently inserted in a body cavity to accomplish the contemplated withdrawal of liquid fluids and the passage thereof into the conduit circuit 126.

In the embodiment shown, the catheter 18 is a small elongated cylindrical element with a passageway 127 extending between the proximal and distal ends thereof. At the distal or suction end of the element, the passage 127 opens to the exterior and provides a fluid inlet 128 where fluids may be sucked into the catheter 18. At its proximal end, the catheter element 18 has a hollow fitting 129 which communicates with and is secured in the discharge end of the passage 127.

The catheter 18 is connected with the canister 19 through a conventional flexible plastic tube length indicated by the line 130 in FIG. 11. At its opposite ends the length is adapted to respectively receive the catheter fitting 129 and the tapered section 105 of the adapter 104 at the fluid inlet 23 of the canister 19.

The body fluids and air sucked into the fluid inlet 128 at the catheter end of the conduit circuit 126 pass through the catheter passageway 127, through the fitting 129 and into the tube length 130. After traversing the tube length 130 under the influence of the vacuum condition established by the pump 13, the fluids pass into the adapter 104, and enter the canister 19 through the fluid inlet 23 provided by the upright lid conduit 103. The liquids entrained in the gases entering the circuit 126 at the catheter end are sucked into the canister and generally separate from the gases and fall out to collect in the reservoir area formed by the jar 85.

The bulk of the liquids remain in the canister and the gases (mainly air) that separate from the liquids in the canister 19 are withdrawn therefrom for reasons of the vacumn condition imposed on the canister 19 by its connection with the vacumn pump 13. These gases pass from the canister 19 through the fluid or suction outlet 24 provided by the upright lid conduit 97.

The canister outlet 24 and the gas intake port 21 of the pump 13 are interconnected in the conduit circuit 126 by means of a gas conduit system designated at 132 in FIG. 11. The gas conduit system 132 includes an exterior gas conduit component 106 that is located at the exterior of the housing 11 and a fixture component 116 of the conduit circuit conduit system 132 that connects the pump intake port 21 with the exterior of the housing 11.

At the exterior of the housing 11, the exterior conduit component 106 of system 132 includes the adapter 99 which communicates with the canister or suction outlet 24, and another flexible plastic tube length 133. In the assembled system 132, the tapered section 101 of adapter 99 is received in one end of the tube length 133 and the fitting 72 at the exterior of the fixture housing 11 is received in the other end of the length 133. As such, the gaseous discharge from the canister 19 passes from the canister through the adapter 99 and then to the fixture component 116 through the elongated plastic tubular length 133. This arrangement provides an air tight exterior passageway from the canister outlet 24 to the fixture component 116 of the conduit system 132.

The fixture component 116 of the conduit system 132 includes the needle valve 16 with its transverse gas passageway 66, the pipe section 71 which is threaded in the gas inlet 26 of the valve assembly 16 and the nut of the exterior fitting 72, and the nipple 64 which communicates at its opposite ends with the gas outlet 25 of the valve 16 and the gas intake port 21 of the pump 13. This arrangement provides a passageway from the exterior of the housing via the fitting 72 to the intake port 21 of the pump 13.

The conduit circuit 126 also includes a gas conduit discharge system 135 for conveying the gases discharged from the pump 13 to a point remote from the fixture 10, and preferably, when the fixture is mounted on the interior wall of an ambulance, to the exterior of the ambulance. The discharge system 135 includes a fitting 136 which is threaded in the gas discharge port 22 of the pump 13 and, at its outer end, received in one end of a conventional elongated flexible plastic tube length 137. At the other end of the tube length 137, the gases are discharged to the atmosphere.

The electrical circuit 131 (FIG. 11) includes the DC motor 14, the switch 15, the 2-wire lead 102 electrically connecting the motor 14 with switch 15, and the 2-wire lead 89 that electrically connects the switch 15 to the 12 V DC power system of the ambulance.

Reference is now made to FIG. 10 and where the fixture 10 is shown as mounted on the inside wall 138 of an ambulance. Wall 138, in part, defines the patient transport area of the ambulance and by means of a vertically extending rib 139 is inwardly offset from the outside or exterior wall 140 of the ambulance. The arrangement of the walls 138 and 140 provides a space 141 therebetween.

The inner wall 138 has an aperture 142 with a predetermined configuration that conforms to that of the rear opening 45 in the housing 11. As seen in FIG. 10, the fixture housing 11 is secured to the inner wall 138 by means of a plurality of fasteners 143 that extend through the holes 35 in the housing flange 32. The arrangement is such that the aperture 142 in the wall and the opening 45 in the housing 11 are aligned and provide an accessway 144 for the passage of the electrical lead 89 and plastic tubular length 137 into the space 141. As apparent from the disclosure above, lead 89 electrically connects the switch 15 to the 12 V DC power supply of the ambulance, and the tubular length connects the outlet port 22 of the pump 13 with the exterior of the vehicle.

While only certain preferred embodiments of this invention have been shown and described by way of illustration, many modifications will occur to those skilled in the art and it is, therefore, desired that it be understood that it is intended herein to cover all such modifications as fall within the true spirit and scope of the invention.

I claim:

1. A fixture for attachment to an internal wall of an ambulance to provide permanently emplaced components of an aspirator for collecting body fluids secreted by a patient being transported thereby, said fixture comprising (A) a housing attachable to the internal wall and having panels that cooperate in defining a cavity located in the interior of said housing and in front of the internal wall when the housing is attached thereto, (B) a diaphragm pump having a gas intake port and being located in the cavity and operable to create a vacuum condition at said gas intake port, (C) an electrical circuit that includes (a) a DC motor located in the cavity and drivingly connected to said pump, and (b) a switch which is located in the cavity and therein connected to said motor and adapted for connection through said internal wall to the DC electrical power supply of the ambulance, said switch having means located at the exterior of said housing and in front of one of said panels and thereat being manipulatable to electrically energize and de-energize said motor when connected to the DC electrical power supply of the ambulance, and (D) gas conduit means communicating with said gas intake port and the exterior of said housing including
  (a) a valve with a passageway located in said cavity and therein having a gas inlet and a gas outlet, said valve having means which is located at the exterior of said housing and in front of one of said panels and thereat being manipulatable to regulate the flow of gas through said passageway, and
  (b) conduit means communicating with and interconnecting said gas intake port and said gas outlet, and
  (c) conduit means connected to said gas inlet and communicating with the exterior of said housing.

2. A fixture in accord with claim 1 further comprising
(E) a bracket mounted at the exterior of said housing and on one of said panels for supporting a canister in front thereof.

3. A fixture in accord with claim 2 wherein
said bracket has a pair of horizontally oriented and horizontally spaced apart arms which are adapted to embrace a canister therebetween and to restrict lateral movements thereof.

4. A fixture in accord with claim 3 wherein said arms are adapted by deformation to embrace and restrict lateral movements of canisters which have differing transverse dimensions and are individually supportable by said bracket.

5. A fixture in accord with claim 2 wherein
said bracket has means for underlying and supporting a canister, and a pair of horizontally oriented and horizontally spaced apart arms which, spacedly above said underlying means, are adapted to therebetween embrace a canister supported thereby.

6. A fixture in accord with claim 1 wherein the panel with the manipulatable switch means located at the front thereof is arranged at an obtuse angle at the exterior of the housing and with respect to the internal wall of the ambulance when the housing is attached thereto.

7. A fixture in accord with claim 1 wherein the panel with the valve manipulating means located in front thereof is arranged at an obtuse angle at the exterior of the housing and with respect to the internal wall of the ambulance when the housing is attached thereto.

8. A fixture in accord with claim 2 where the panel on which the bracket is mounted is arranged at an obtuse angle at the exterior of the housing and with respect to the internal wall of the ambulance when the housing is attached thereto.

9. A fixture for attachment to an internal wall of a motorized ambulance to provide permanently emplaced components of an aspirator system for collecting body fluids secreted by a patient being transported thereby, said fixture comprising
(A) a housing attachable to the internal wall and having panels that cooperate in defining a cavity located in the interior of said housing and in front of the internal wall when the housing is attached thereto, said housing having a rear side and means thereat defining an opening providing access to said cavity from the exterior of said housing,
(B) a diaphragm pump having a gas intake port and a gas discharge port, and being located in the cavity and operable to create a vacuum condition at said gas intake port,
(C) an electrical circuit that includes
  (a) a DC motor located in the cavity and drivingly connected to said pump, and
  (b) a switch which is located in the cavity and therein connected to said motor, said switch being adapted for connection through said internal wall to the DC electrical power supply of the ambulance, said switch having means located at the exterior of said housing and in front of one of said panels and being thereat manipulatable to electrically energize and de-energize said motor when connected to the DC electrical power supply of the ambulance, and
(D) gas conduit means communicating with said gas intake port and the exterior of said housing including
  (a) a valve with a passageway located in said cavity and therein having a gas inlet and a gas outlet, said valve having means which is located at the exterior of said housing and in front of one of said panels and thereat being manipulatable to regulate the flow of gas through said passageway, and said gas outlet of said valve and said gas intake Port of said pump being arranged in close proximity and axially aligned, and
  (b) conduit means communicating with and interconnecting said gas intake port and said gas outlet,
  (c) a conduit element located at the exterior of said housing for receiving gases destined for passage to said pump, and
  (d) a conduit communicating with and interconnecting said gas inlet of said valve and the exteriorly located conduit element, and
(E) gas conduit means communicating with said gas discharge port and being adapted for extension through said opening to the exterior of said housing.

10. The combination comprising
(A) a housing attachable to the internal wall of an ambulance with a DC electrical power supply so as to provide a Permanent mounting emplacement for components of an aspirator system when said housing is attached to said internal wall, said housing having panels that cooperate in defining a cavity located in the interior of said housing and in front of the internal wall when the housing is attached thereto, said housing having a rear side and means thereat defining an opening providing access to said cavity from the exterior of said housing, and
(B) an aspirator system adapted for use in collecting body fluids secreted by a patient being transported by the ambulance and having components that include
  (a) a diaphragm pump having a gas intake port and being located in said cavity and operable to create a vacuum condition at said gas intake port,
  (b) an electrical circuit that includes
    (1) a DC motor located in the cavity and drivingly connected to said pump, and
    (2) a switch which is located in the cavity and therein connected to said motor, said switch being adapted for connection through said internal wall to the DC power supply of the ambulance, said switch having means located at the exterior of said housing and in front of one of said panels and being thereat manipulatable to electrically energize and de-energize said motor when connected to the DC electrical power supply,
  (c) a gas conduit system communicating with said gas intake port and the exterior of said housing including
    (1) a valve having a passageway located in said cavity and therein having a gas inlet and a gas outlet, said valve having means located at the exterior of said housing and in front of one of said panels and being manipulatable thereat to control the vacuum condition in said passageway of said valve when said motor is energized, (2) a conduit located in said cavity which interconnects and communicates with said gas outlet of said valve and said intake port of said pump, (3) a conduit element located at the exterior of said housing for receiving gases destined for passage to said pump, and (4) a conduit connected in said cavity with said gas inlet of said valve and being connected to and communicating with the exteriorly located conduit element, (d) a pressure gauge mounted on one of said panels and being viewable from the exterior of said housing, said gauge having means in said cavity that communicates with the passageway of said valve for sensing the vacuum condition thereat, (e) a replaceable canister providing a reservoir for collecting body fluids aspirated from a patient, said canister having a fluid inlet and a suction outlet, (f) a bracket supporting said canister at the exterior of said housing and thereat being mounted on and in front of one of said panels, the last mentioned one of said panels being arranged at an obtuse angle at the exterior of the housing and with respect to the internal wall of the ambulance when the housing is attached thereto, and (g) a gas conduit system communicating with and interconnecting the suction outlet of said canister with said conduit element.

11. The combination in accord with claim 10 wherein said aspirator system further includes (h) a replaceable catheter which is insertable in a body cavity of a patient for receiving fluids therein, and (i) replaceable conduit means connecting said catheter with said fluid inlet of said canister.

12. In a motorized ambulance having a DC electrical power supply and internal and external walls which are spaced apart, the improvement comprising (A) an internal wall section that, at least in part, defines a patient transport area in the ambulance and has an aperture with a predetermined configuration that provides a wall opening between said transport area and the space between said internal wall section and the external wall of the ambulance, (B) a fixture mounted on said wall section to Provide permanently emplaced components of an aspirator for collecting body fluids secreted by a Patient being transported by the ambulance, said fixture having components that include (a) a housing attached to said internal wall section, said housing having panels that cooperates in defining a cavity located in the interior of said housing and in front of the internal wall of the transport area, said housing having a rear side and means thereat defining a cavity opening into the cavity and which is so oriented with respect to said aperture as to provide access to said cavity from the space between said internal wall section and the external wall of the ambulance, (b) a diaphragm pump having a gas intake port and a gas discharge port and being located in the cavity and operable to create a vacuum condition at said gas intake port, (c) an electrical circuit that includes (1) a DC motor located in the cavity and drivingly connected to said pump, (2) electrical conduit means extending through said wall and cavity openings from the cavity and into the wall space between said internal wall section and the external wall of the ambulance and being electrically connected to the DC electrical power supply of said ambulance at the exterior of said housing, and (3) an electrical switch which is connected in the cavity to said electrical conduit means and to said motor, said switch having means located at the exterior of the housing and thereat being manipulatable to electrically energize and de-energize said motor, and (d) a bracket mounted at the exterior of said housing and on a first of said panels for supporting a canister with a fluid inlet for entrained body fluids and a suction outlet, said bracket being adapted to support said canister in front of, and in close proximity to, said first panel, and (e) gas conduit means communicating with said gas intake port and the exterior of said housing, said gas conduit means including (1) a valve with a passageway located in said cavity and having a gas inlet and a gas outlet, said valve having means located in front of a second of said panels and thereat being manipulatable to regulate the flow of gas through said passageway, (2) conduit means communicating with and interconnecting said gas intake port and said gas outlet, and (3) conduit means communicating in the cavity with said gas inlet of said valve and being adapted at the exterior of said housing to communicate with the suction outlet of a canister supported by said bracket, and (f) gas conduit means communicating with said gas discharge port of said pump and with the exterior of said housing, the last mentioned gas conduit means being connected to the pump in said cavity and extending through said wall and cavity openings and into the wall space between said internal wall section and the external wall of the ambulance.

13. The improvement in accord with claim 12 wherein said electrical switch is mounted on said second panel, said second panel is arranged at an obtuse angle at the exterior of the housing and with respect to said wall panel section, and said first panel is arranged at an obtuse angle at the exterior of the housing and with respect to said wall panel section.

14. The improvement in accord with claim 12 wherein said valve and said pump are arranged in close proximity and with the gas outlet of the valve axially aligned with the gas intake port of said pump.

15. In a motorized ambulance having a DC electrical power supply and internal and external walls which are spaced apart, the improvement comprising (A) an internal wall section that, at least in part, defines a patient transport area in the ambulance and has an aperture with a predetermined configuration that provides a wall opening between said transport area and the space between said internal wall section and the external wall of the ambulance, (B) a fixture mounted on said wall section to provide permanently emplaced components of an aspirator for collecting body fluids secreted by a patient being transported by the ambulance, said fixture having components that include
- (a) a housing located in the patient transport area and being attached to said internal wall section, said housing having a rear side that confronts said internal wall section, a cavity located in the interior of the housing, and a cavity opening that is located at said rear side and so oriented with respect to said wall opening as to provide access between said cavity and the space between said internal wall section and the external wall of the ambulance,
- (b) a diaphragm pump mounted in said cavity and having a gas intake port and a gas discharge port,
- (c) an electrical circuit that includes
  - (1) a DC motor located in said cavity and drivingly connected to said pump,
  - (2) electrical conduit means extending through said wall and cavity openings and being connected to the DC electrical power supply of said ambulance, and
  - (3) an electrical switch which is mounted on said housing and connected in the cavity to said electrical conduit means and to said motors said switch having means that is located at the exterior of said housing and thereat being manipulatable to electrically energize and de-energize said motor,
- (d) gas conduit means communicating with said gas intake port and the exterior of said housing including
  - (1) a valve having a gas inlet and a gas outlet located in said cavity and means at the exterior of said housing and thereat manipulatable to regulate the flow of gas between said gas inlet and said gas outlet,
  - (2) conduit means communicating with and interconnecting said gas intake port and said gas outlet, and
  - (3) conduit means connected to said gas inlet and communicating with the exterior of said housing, and
- (e) gas conduit means connecting the gas discharge port of said pump with the exterior of said housing and extending through said wall and cavity openings between said cavity and the space between said internal wall section and the external wall of the ambulance.

\* \* \* \* \*